United States Patent [19]

Williams

[11] Plant 4,091

[45] Aug. 16, 1977

[54] MINIATURE ROSE PLANT

[75] Inventor: Ernest D. Williams, Dallas, Tex.

[73] Assignee: Ralph S. Moore, Visalia, Calif. ; a part interest

[21] Appl. No.: 725,081

[22] Filed: Sept. 17, 1976

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

A novel miniature rose variety characterized by its red-orange to orange-pink blossoms.

1 Drawing Figure

1

The present invention relates to a new and distinct variety of hardy, dwarf, bush type rose plant of the miniature class; the variety being primarily characterized — as to novelty — by bright orange pink buds and flowers which in general color effect are similar to Mary Marshall (miniature — U.S. Plant Pat. No. 3,346).

The variety is further characterized by:

An abundance of bloom with flowers borne singly or several to stem in loose clusters.

Some fragrance.

A plant which is vigorous, of rounded upright shape and mat, medium — small foliage with pointed leaflets; the buds and flowers being similar in form to Mary Marshall but of slightly smaller size.

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Miss Hillcrest as the seed parent (U.S. Plant Pat. No. 3,027), and Mabel Dot (miniature — not patented) as the pollen parent.

Subsequent to origination of the variety I successfully asexually reproduced it, by cuttings, in my nursery located as aforesaid — also it has been reproduced at the Sequoia Nursery (Ralph S. Moore), Visalia, Calif., the reproductions having run true in all respects.

The color photograph illustrates the variety, including foliage, buds and flowers. Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf; bushy; seedling; greenhouse; outdoors; cut flowers; garden decoration; potted plant.

Class: Miniature. Variety name: 'Hula Girl.'

Flowers: Continuity: continuous — repeat bloom all season. Fragrance: slight to moderate.

Flowers borne: Singly and several together (three to five) on sturdy, wirey, medium length stems.

2

Quantity of bloom: Abundant both outside and in greenhouse.

Bud:

*Peduncle.*—Medium length; slender but sturdy; erect; medium green; hairs — may be some very short.

*Before calyx breaks.*—Size — small. Form: medium long; pointed with several foliaceous appendages and some hairs on surface of bud; with foliaceous parts extending beyond the tip of the bud equal to one-half or less of its length. Color — medium green.

*As calyx breaks.*—Color — orange-pink to Poppy Red 16/1; opens: same general color. Size — small.

Bloom:

*Size when fully open.*—Small, averaging about 30 to 35 mm.

*Petalage.*—Double 40–45 petals, arranged regularly.

*Form.*—Full; high center at first, becoming more rounded, with petals rolled loosely outward, and later at maturity petals become folded at tips to give a pointed effect.

Petals: Thick; satiny on inside and on outside surface.

*Shape.*—Outside petals, broad lanceolate with rounded tip; intermediate — broad lanceolate with acute tip; inside — lanceolate with acute tip.

Color: Newly opened flower from a plant grown in plastic greenhouse (August, 1976), Visalia, Calif.

*Outside petal.*—Outside surface — near Poppy Red 16/1 with both lighter and darker areas (or veining), thence shading lighter toward the base and blending into yellow, becoming yellow at base; inside surface — near Poppy Red 16/1, similar to outside surface, thence shading lighter toward base and blending into yellow, becoming yellow at base.

*Intermediate petal.*—Outside surface — similar to outside petal, but red shade may be darker (near Vermillion 18/1 or lighter). Inside surface — similar to outside petal, but red shade may be darker (near Vermillion 18/1 or lighter).

*Inner Petal.*—Outside surface — same as intermediate petal; inside surface — same as intermediate petal. General color effect newly opened flowers — bright orange to orange pink. Three days open — color similar to newly opened flowers but lighter shade (similar to Azalea Pink 618). Behavior — Opens well in all weather. Spent petals may persist for short time then drop off (the bud and flower color may vary — at times the color may be similar to Azalea Pink 618). Flower longevity (May 1976) — plant in pot 5–7 days or longer. Cut flowers at living room temperature 4–7 days.

Reproductive organs:

*Stamens.*—Few or none.

*Filaments.*—Few or none. Very short.

*Anthers.*—Dark — orange red.

*Pollen.*—Little or none.

*Pistils.*—Average number.

*Styles.*—Very short.

*Stigma.*—Dark; reddish.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; abundant; medium small; leathery; mat.

*Leaflets.*—Shape: broad lanceolate; apex acute; base rounded or rounded acute. Margin serrate. Color: medium green; new growth — reddish.

*Rachis.*—Medium strength; upper side usually smooth but may have a few tiny short hairs and/or prickles, grooved; underside sparsely thorny with few or no tiny prickles.

*Stipules.*—Medium long; narrow to medium width, fairly short narrow points which turn out usually at about 45° or more.

*Growth.*—Habit — dwarf; bushy; upright; much branched. Growth — free vigorous. Canes — medium; slender; sturdy. Main Stems — color: medium green. Thorns: moderately thorny: usually small; straight, inclined slightly downward; color: brown. Prickles — none. Hairs — none. Branches — color: medium green. Thorns: moderately thorny; short length; slender; nearly straight inclined slightly downward. Medium to short oval base. Prickles: none. Hairs: none. New shoots — color: medium green (may be slightly reddish outdoors). Thorns: moderately thorny; color: reddish; straight inclined slightly downward. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, essentially as illustrated and described, characterized by buds and flowers of a bright red-orange to orange-pink color resembling the Mary Marshall miniature rose (U.S. Plant Pat. No. 3,346), the buds and flowers being slightly smaller in size than Mary Marshall; and further characterized by a plant which is vigorous and compact, said plant being easy to propagate from cuttings, with medium small, disease resistant, mat foliage, an abundance of bloom, with better than average keeping quality, with flowers borne singly or several to the stem in loose clusters.

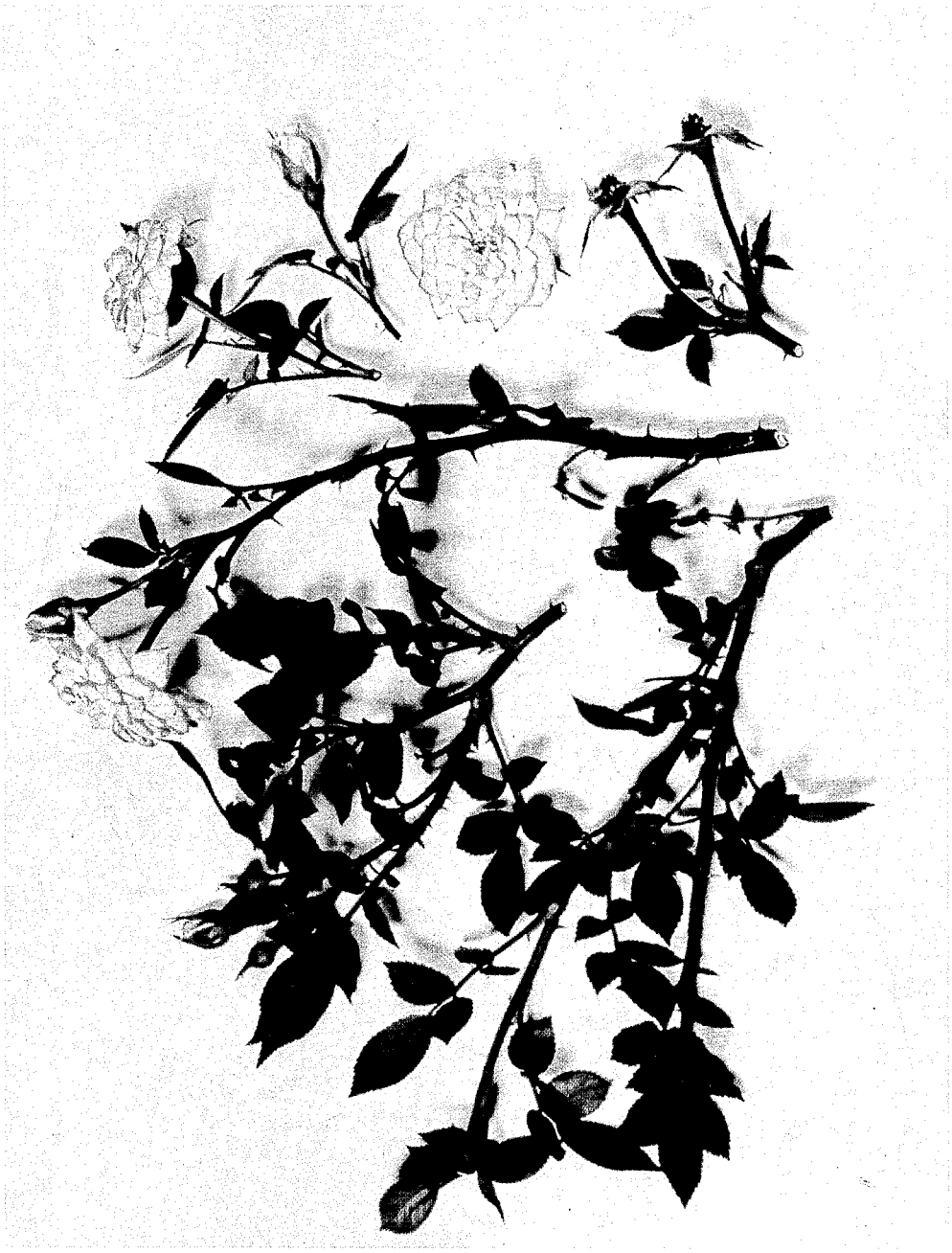

* * * * *